(12) United States Patent
Jayavanth et al.

(10) Patent No.: US 9,669,235 B2
(45) Date of Patent: Jun. 6, 2017

(54) PHOTOTHERAPY SYSTEM THAT ADAPTS TO THE POSITION OF AN INFANT IN NEONATAL CARE

(71) Applicant: KONINKLIJKE PHILIPS N.V., Eindhoven (NL)

(72) Inventors: Sanjay Jayavanth, Bangalore (IN); Anil Shivram Raiker, Goa (IN); Shrutin Ulman, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 66 days.

(21) Appl. No.: 14/417,982

(22) PCT Filed: Jul. 30, 2013

(86) PCT No.: PCT/IB2013/056250
§ 371 (c)(1),
(2) Date: Jan. 28, 2015

(87) PCT Pub. No.: WO2014/024092
PCT Pub. Date: Feb. 13, 2014

(65) Prior Publication Data
US 2015/0190651 A1    Jul. 9, 2015

(30) Foreign Application Priority Data
Aug. 8, 2012 (IN) .............. 3255/CHE/2012

(51) Int. Cl.
*A61N 5/06* (2006.01)
*A61G 11/00* (2006.01)

(52) U.S. Cl.
CPC ............ *A61N 5/0621* (2013.01); *A61G 11/00* (2013.01); *A61G 2203/44* (2013.01); *A61G 2203/46* (2013.01); *A61N 2005/0626* (2013.01); *A61N 2005/0637* (2013.01); *A61N 2005/0638* (2013.01); *A61N 2005/0652* (2013.01)

(58) Field of Classification Search
CPC ....... A61G 11/00; A61N 5/0621; A61N 5/613
See application file for complete search history.

(56) References Cited

U.S. PATENT DOCUMENTS

| | | | | |
|---|---|---|---|---|
| 6,409,654 B1 * | 6/2002 | McClain | ................ | A61G 11/00 5/655 |
| 6,615,061 B1 * | 9/2003 | Khalil | .................... | G01N 21/49 600/310 |
| 8,048,136 B2 * | 11/2011 | Chung | ................. | A61N 5/0621 607/88 |
| 8,337,538 B1 * | 12/2012 | Ford | .................... | A61N 5/0621 607/88 |

(Continued)

FOREIGN PATENT DOCUMENTS

GB    2216012 A    10/1989
WO    2006135865 A2    12/2006

*Primary Examiner* — Lynsey Crandall
*Assistant Examiner* — Amanda Steinberg

(57) ABSTRACT

Systems and methods for providing phototherapy to an infant use the determined position and/or posture of an infant to provide effective phototherapy through a set of light sources, to avoid electromagnetic radiation from the light sources directly impinging on the eyes of the infant, and to reduce or limit the level of electromagnetic radiation leaked into the environment.

15 Claims, 4 Drawing Sheets

(56) References Cited

U.S. PATENT DOCUMENTS

| | | | |
|---|---|---|---|
| 8,617,043 B2* | 12/2013 | Ten Eyck | A61B 5/11 600/22 |
| 2006/0089546 A1 | 4/2006 | Mahony | |
| 2007/0088410 A1* | 4/2007 | Chung | A61N 5/0621 607/91 |
| 2011/0261182 A1* | 10/2011 | Lee | A61B 5/1079 348/77 |

* cited by examiner

PHOTOTHERAPY SYSTEM THAT ADAPTS TO THE POSITION OF AN INFANT IN NEONATAL CARE

CROSS-REFERENCE TO PRIOR APPLICATIONS

This application is the U.S. National Phase application under 35 U.S.C. §371 of International Application No. PCT/IB2013/056250, filed on Jul. 30, 2013, which claims the benefit Indian Patent Application No. 3255/CHE/2012, filed on Aug. 8, 2012. These applications are hereby incorporated by reference herein.

The present disclosure pertains to systems and methods for providing phototherapy to an infant, and, in particular, to systems and methods that adapt to the position of an infant.

It is well known to treat infants, e.g. neonates, with phototherapy. An example of well-known phototherapy is jaundice treatment using blue light. It is well-known that the type of blue light that is effective for jaundice treatment is potentially harmful when exposed for prolonged periods to the eyes of an infant. It is well-known that exposure to the type of blue light that is effective for jaundice treatment has side-effects for caregivers, including but not limited to nausea.

Accordingly, it is an object of one or more embodiments of the present invention to provide a phototherapy system for an infant. The system comprises an infant-supporting body configured to support an infant on a top-surface thereof; one or more sensors that generate one or more output signals conveying information related to a position of the infant on the top-surface of the infant-supporting body; a set of light sources carried by the infant-supporting body, wherein the set of light sources are configured and arranged such that, responsive to activation of a subset of the set of light sources, electromagnetic radiation emitted by the subset of the set of light sources is guided through the top-surface of the infant-supporting body; and one or more processors configured to execute computer program modules. The computer program modules comprise a position module configured to determine the position of an infant on the top-surface of the infant-supporting body, wherein the determination is based on information from the one or more sensors; and a light module configured to control one or more subsets of light sources of the set of light sources based on the determined position of the infant such that the emitted electromagnetic radiation provides phototherapy for the infant.

It is yet another aspect of one or more embodiments of the present invention to provide a method for providing phototherapy to an infant. The method comprises supporting an infant on a top-surface of an infant-supporting body; generating one or more output signals conveying information related to a position of the infant on the top-surface of the infant-supporting body; emitting electromagnetic radiation through the top-surface of the infant-supporting body from a set of light sources; determining the position of the infant on the top-surface of the infant-supporting body based on information from one or more sensors; and controlling one or more subsets of light sources from the set of light sources based on the determined position of the infant such that the emitted electromagnetic radiation provides phototherapy for the infant.

It is yet another aspect of one or more embodiments to provide a system configured to providing phototherapy to an infant. The system comprises means for supporting an infant on a top-surface of an infant-supporting body; means for generating one or more output signals conveying information related to a position of the infant on the top-surface of the infant-supporting body; means for emitting electromagnetic radiation through the top-surface of the infant-supporting body; means for determining the position of the infant on the top-surface of the infant-supporting body based on information from one or more sensors; and means for controlling the means for emitting electromagnetic radiation based on the determined position of the infant such that the emitted electromagnetic radiation provides phototherapy for the infant.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

Figure 3:
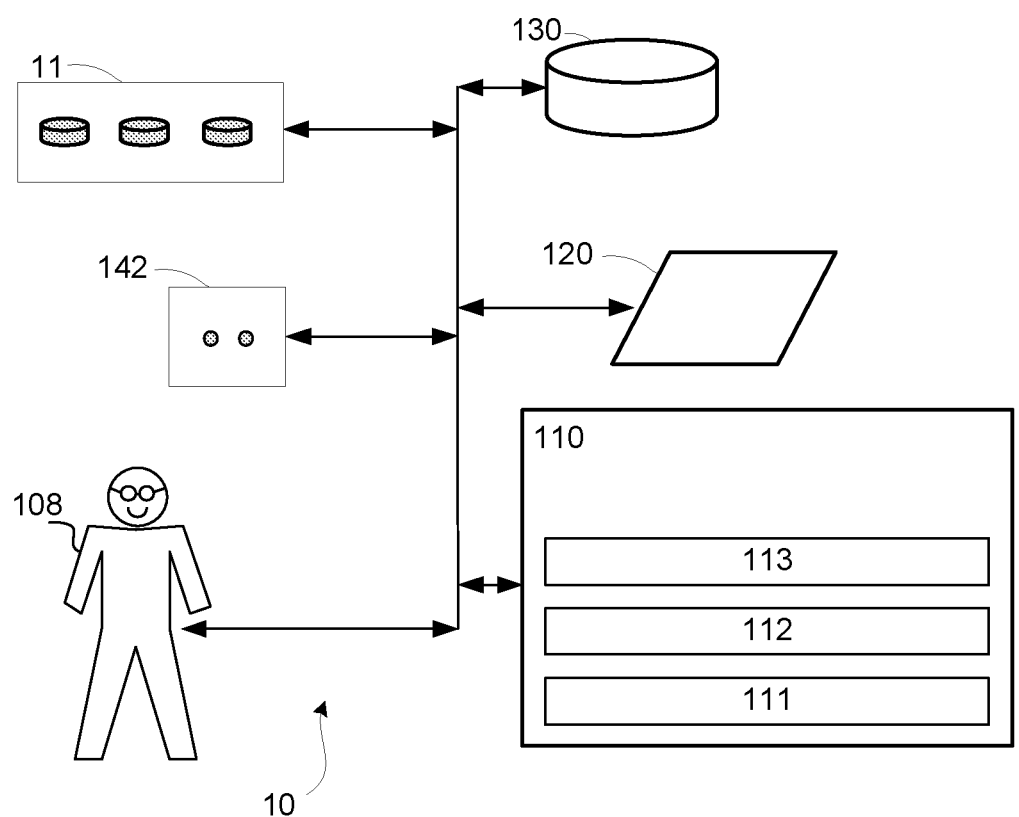
Figure 4:
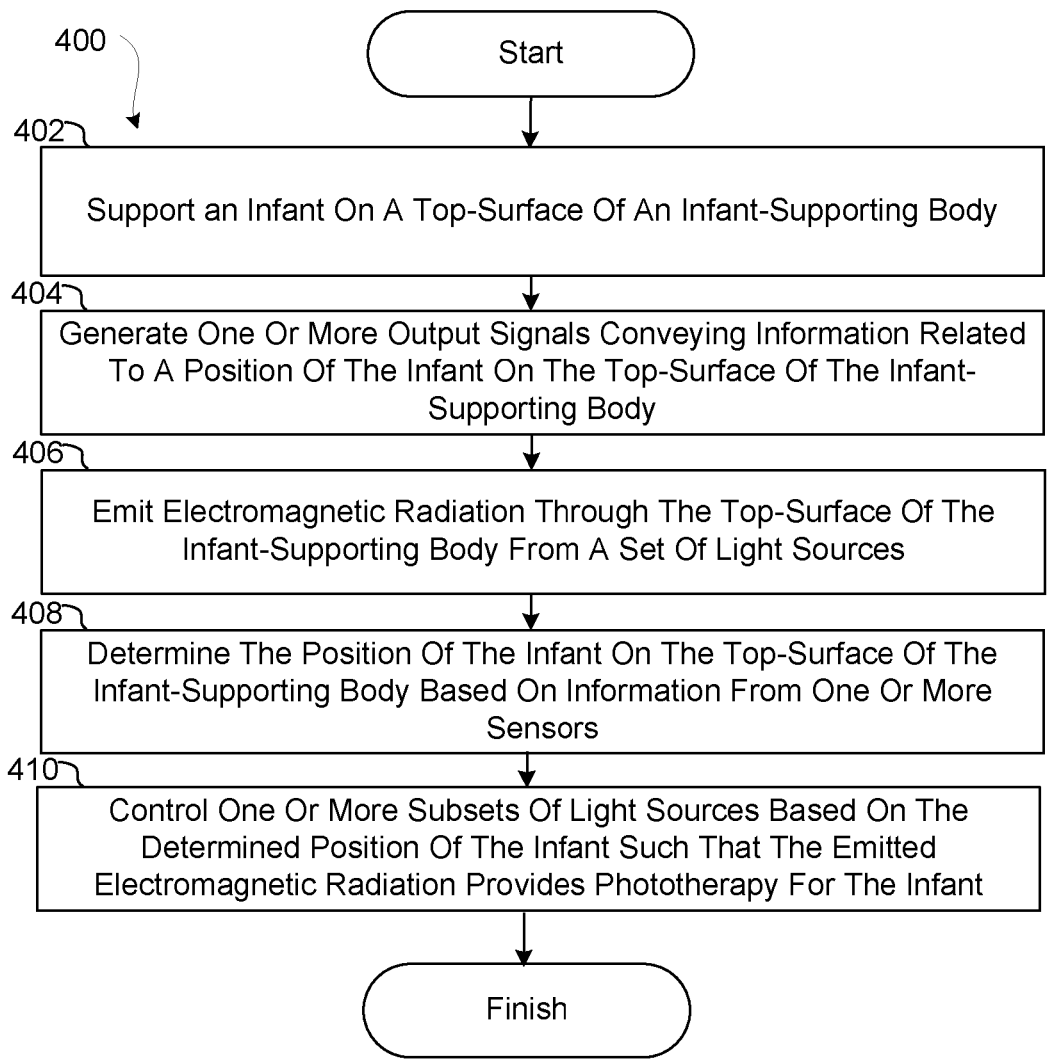

FIG. 3 schematically illustrates a phototherapy system in accordance with one or more embodiments; and FIG. 4 illustrates a method for providing phototherapy in accordance with one or more embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
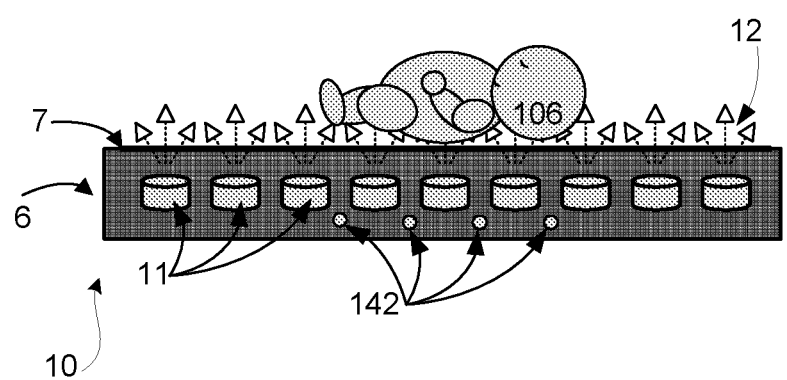
FIG. 1 illustrates a side view of a phototherapy system in accordance with one or more embodiments.

FIG. 1 illustrates a side view of a phototherapy system 10 in accordance with one or more embodiments. System 10 may include one or more of an infant-supporting body 6, one or more sensors 142, a set of light sources 11, a position module 111, a light module 112, and/or other components. Infant-supporting body 6 may include a top-surface 7 and be configured to support on infant 106 on top-surface 7. Top-surface 7 may engage infant 106 during use of system 10. Infant-supporting body 6 may be configured to carry a set of light sources 11.

Phototherapy may be used to treat jaundice (or hyperbilirubinemia) by reducing the level of bilirubin. Effective and/or appropriate levels of phototherapy may be based on an infant's age, size, weight, and/or other physiological, environmental, and/or infant-specific parameters. Phototherapy may use electromagnetic radiation having a peak wavelength between, e.g., 460 nm and 500 nm, an emission spectrum ranging from, e.g., 400 nm to 520 nm, and preferably using a narrow bandwidth delivered at an irradiance of, e.g., 30-35 $\mu W/cm^2/nm$ to, e.g., up to 80% of an infant's body surface area (BSA). Phototherapy may potentially need to be kept from directly impinging on the eyes of the infant, e.g. by making the infant wear goggles. Exposure to the type of blue light that is effective for jaundice treatment may have side-effects for caregivers, including, but not limited to, headache, nausea, and/or vertigo.

Infant-supporting body 6 of system 10 in FIG. 1 may be configured to engage with and/or carry a set of light sources 11, such that, responsive to activation of some or all of the set of light sources 11, electromagnetic radiation 12 emitted by light sources 11 is guided through top-surface 7. Emitted electromagnetic radiation 12 may directly impinge on infant 106 and thus provide phototherapy for infant 106.

Infant 106 may be monitored while on or near system 10 or a component thereof, e.g. while undergoing phototherapy.

One or more sensors 142 of system 10 in FIG. 1 may be configured to generate output signals conveying information related to the age, position, posture, size, weight, and/or status of infant 106, physiological, environmental, and/or infant-specific (medical) parameters related to infant 106, and/or other information. System 10 may use any of the generated output signals to monitor infant 106. In some embodiments, the conveyed information may be related to parameters associated with the state and/or condition of infant 106, the breathing of infant 106, the gas breathed by infant 106, the heart rate of infant 106, the respiratory rate of infant 106, vital signs of infant 106, including one or more temperatures, oxygen saturation of arterial blood ($SpO_2$), whether peripheral or central, and/or other parameters.

As a non-limiting example, one or more sensors 142 may generate one or more output signals conveying information related to a (three-dimensional) position of infant 106 on top-surface 7, e.g. through stereoscopy. In some embodiments, one or more sensors 142 may be configured to generate output signals conveying information related to whether the eyes of infant 106 are opened or closed, and/or whether the eyes of infant 106 are facing away from top-surface 7. During phototherapy, it is preferred that emitted electromagnetic radiation from light sources 11 substantially does not directly impinge on the eyes of infant 106. Sensors 142 may include one or more of a temperature sensor, a pressure/weight sensor, a light sensor, one or more still-image cameras, one or more video cameras, and/or other sensors.

In some embodiments, sensors 142 may be configured to generate output signals conveying information related to a level of bilirubin in infant 106. Such sensors may for example be used to perform interstitial fluids bilirubin measurements.

Leaked electromagnetic radiation, e.g. from light sources 11, which does not impinge on infant 106 does not substantially contribute to the phototherapy for infant 106. Such electromagnetic radiation may leak into the environment and could bother a caregiver 108 (such as, e.g., a nurse, a doctor, a healthcare professional, etc.). In some embodiments, one or more (light) sensors may be configured to generate one or more output signals conveying information related to a level and/or amount of leaked electromagnetic radiation emitted, e.g., by the set of light sources 11.

The illustration of sensor 142 including four members in FIG. 1 is not intended to be limiting. System 10 may include one or more sensors. Resulting signals or information from one or more sensors 142 may be transmitted to processor 110, user interface 120, electronic storage 130, and/or other components of system 10. This transmission can be wired and/or wireless.

Monitoring of infant 106 may be based on one or more sensors 142 and/or any of the related parameters described herein. Monitoring and/or measuring may be used as a contact-less, non-invasive means to obtain information. "Contact-less" refers to either refraining from the use of adhesives (e.g. on the skin of infant 106) and/or refraining from direct skin contact in the context of this disclosure.

Figure 2:
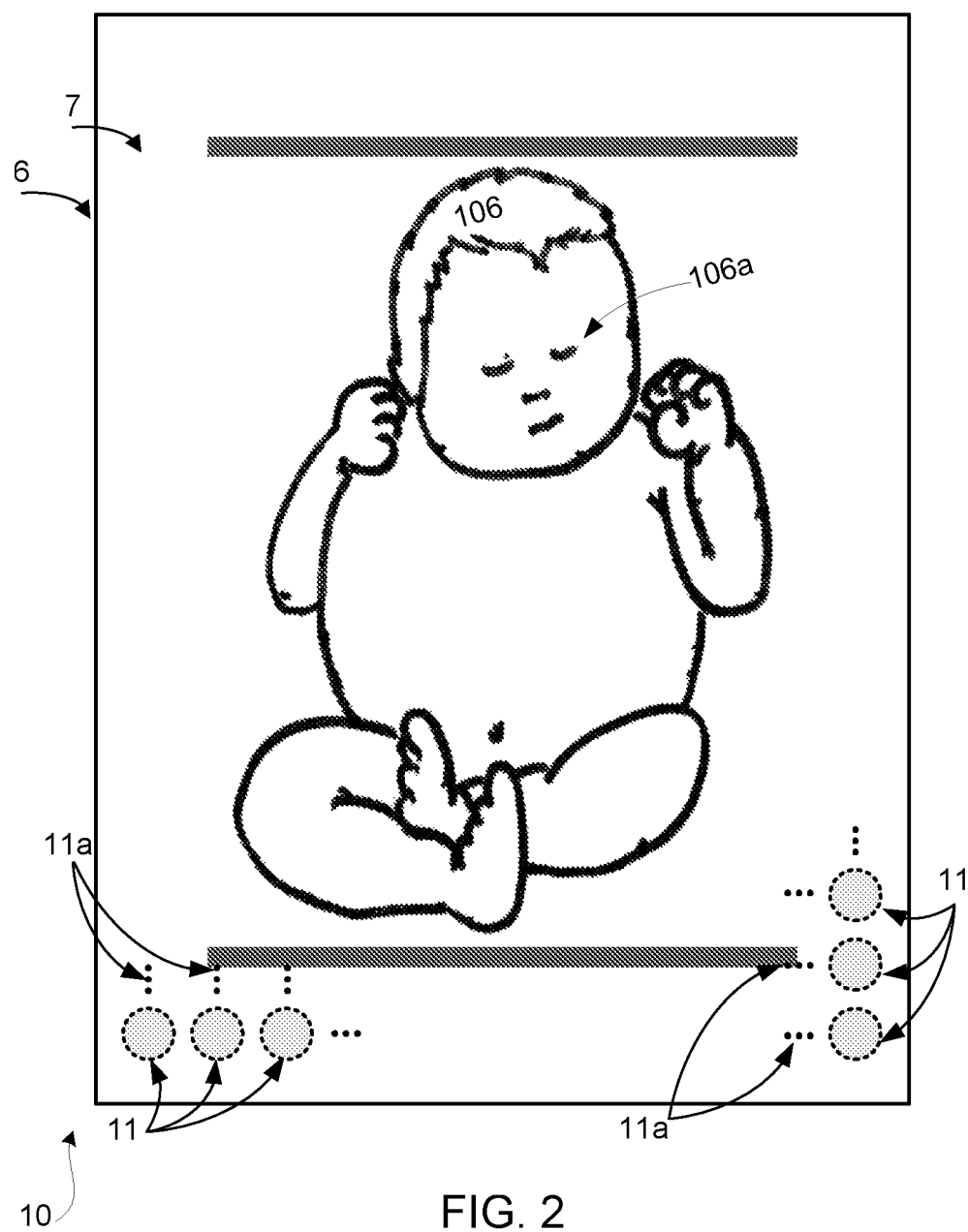
FIG. 2 illustrates a top view of a phototherapy system in accordance with one or more embodiments.

One or more light sources 11 of system 10 in FIG. 1 may be configured such that electromagnetic radiation 12 emitted by the one or more light sources is guided through top-surface 7. Individual light sources may include one or more of an LED, OLED, and/or other source of electromagnetic radiation. Light sources 11 may be arranged in a regular pattern, irregular pattern, or combination of both. For example, light sources 11 may be arranged in a regular grid. By way of illustration, FIG. 2 illustrates a top-view of system 10. The depiction of three light sources 11 underneath the bottom left corner of top-surface 7 is not meant to be limiting, but to be exemplary. The depiction of three light sources 11 underneath the bottom right corner of top-surface 7 is not meant to be limiting, but to be exemplary. Ellipses 11a indicate additional light sources that may be arranged underneath top-surface 7, horizontally, vertically, diagonally, and/or in multiple directions, e.g. to create a regular grid of light sources. Light sources 11 may extend underneath the entire top-surface 7 of infant-supporting body 6, including under infant 106.

Referring to FIG. 1, light sources 11 of system 10 may be configured to have a controllable level of intensity (e.g. denoted by a percentage of the maximum available level of intensity for an individual light source), a controllable direction and/or angle of illumination (as depicted by multiple directions of electromagnetic radiation 12 for individual light sources in FIG. 1), a controllable selection of illumination spectra, and/or other controllable illumination characteristics and/or illumination parameters. For example, illumination parameters of a light source 11 may be controlled by adjusting optical components within the light source, including, but not limited to, one or more of refractive components, reflective components, lenses, mirrors, filters, polarizers, diffraction gradients, optical fibers, and/or other optical components. Individual light sources 11 may be controlled such that only part of (the exposed skin of) infant 106 is illuminated. Particularly, part of (the exposed skin of) infant 106 that is not near the eyes of infant 106.

Note that electromagnetic radiation emitted by real-world light sources, as opposed to theoretical models of light sources, may have a non-deterministic distribution of its intensity and/or (beam) direction, at least for practical applications of phototherapy and/or digital image processing. Note furthermore that guiding, reflecting, and/or scattering a beam of electromagnetic radiation may be considered a stochastic event governed by a probability distribution. Nonetheless, electromagnetic radiation may be considered to substantially directly impinge on or near a particular surface and/or location if at least about 90%, at least about 95%, about 99%, and/or another percentage of the emitted radiation directly so impinges.

FIG. 3 schematically illustrates a phototherapy system 10 in accordance with one or more embodiments. User interface 120 of system 10 in FIG. 3 may be configured to provide an interface between system 10 and a user (e.g., user 108, a caregiver, a healthcare provider, a therapy decision-maker, etc.) through which the user can provide information to and/or receive information from system 10. This enables data, results, and/or instructions and any other communicable items, collectively referred to as "information," to be communicated between the user and system 10. An example of information that may be conveyed to user 108 is a report detailing the changes in monitored vital signs throughout a period during which infant 106 is present within system 10. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 by user interface 120 in the form of auditory signals, visual signals, tactile signals, and/or other sensory signals, or any combination thereof.

By way of non-limiting example, user interface 120 may include a radiation source capable of emitting light. The radiation source may include, for example, one or more of at least one LED, at least one light bulb, a display screen, and/or other sources. User interface 120 may control the radiation source to emit light in a manner that conveys to user 108 information related to the leaked level of electromagnetic radiation.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 10 from removable storage (e.g., a smart card, a flash drive, a removable disk, etc.) that enables the user(s) to customize the implementation of system 10. Other exemplary input devices and techniques adapted for use with system 10 as user interface 120 include, but are not limited to, an RS-232 port, RF link, an IR link, modem (telephone, cable, Ethernet, internet or other). In short, any technique for communicating information with system 10 is contemplated as user interface 120.

Electronic storage 130 of system 10 in FIG. 3 comprises electronic storage media that electronically stores information. The electronic storage media of electronic storage 130 may include one or both of system storage that is provided integrally (i.e., substantially non-removable) with system 10 and/or removable storage that is removably connectable to system 10 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 10 to function properly. For example, electronic storage 130 may record or store information related to the provided phototherapy, and/or other information. Electronic storage 130 may be a separate component within system 10, or electronic storage 130 may be provided integrally with one or more other components of system 10 (e.g., processor 110).

Processor 110 of system 10 in FIG. 3 is configured to provide information processing capabilities in system 10. As such, processor 110 includes one or more of a digital processor, an analog processor, a digital circuit designed to process information, an analog circuit designed to process information, a state machine, and/or other mechanisms for electronically processing information. Although processor 110 is shown in FIG. 3 as a single entity, this is for illustrative purposes only. In some implementations, processor 110 includes a plurality of processing units.

As is shown in FIG. 3, processor 110 is configured to execute one or more computer program modules. The one or more computer program modules include one or more of a parameter determination module, a position module 111, a light module 112, a therapy module 113, and/or other modules. Processor 110 may be configured to execute modules 111, 112, and/or 113 by software; hardware; firmware; some combination of software, hardware, and/or firmware; and/or other mechanisms for configuring processing capabilities on processor 110.

It should be appreciated that although modules 111, 112, and 113 are illustrated in FIG. 3 as being co-located within a single processing unit, in implementations in which processor 110 includes multiple processing units, one or more of modules 111, 112, and/or 113 may be located remotely from the other modules. The description of the functionality provided by the different modules 111, 112, and/or 113 described below is for illustrative purposes, and is not intended to be limiting, as any of modules 111, 112, and/or 113 may provide more or less functionality than is described. For example, one or more of modules 111, 112, and/or 113 may be eliminated, and some or all of its functionality may be provided by other ones of modules 111, 112, and/or 113. Note that processor 110 may be configured to execute one or more additional modules that may perform some or all of the functionality attributed below to one of modules 1111, 112, and/or 113.

A parameter determination module of system 10 (not shown) may be configured to determine one or more status parameters, medical parameters, and/or other parameters from output signals generated by sensor(s) 142. Parameters may be related to an infant's age, size, volume, weight, and/or other physiological, environmental, and/or infant-specific parameters. One or more status parameters may be related to the presence, posture, and/or position of infant 106. One or more medical parameters may be related to monitored vital signs of infant 106, and/or other medical parameters of infant 106. Other parameters may be related to the environment near system 10, such as, e.g., air temperature. Some or all of this functionality may be incorporated or integrated into other computer program modules of processor 110.

Position module 111 of system 10 in FIG. 3 may be configured to determine the presence, (three-dimensional) position, posture, and/or orientation of infant 106 (and/or anatomical parts including but not limited to the eyes, one or more legs, one or more arms, head, forehead, and/or other anatomical parts of infant 106). The determination by position module 111 may be based on information from one or more sensors 142, such as information from, e.g., one or more weight sensors, and/or through stereoscopy using multiple cameras. In some embodiments, position module 111 may be configured to determine in which area (and/or in which posture and/or orientation) on top-surface 7 of infant-supporting body 6 exposed skin of infant 106, e.g. the head or feet of the infant, is currently located, such that light sources 11 may be controlled accordingly. Note that phototherapy through clothing or a diaper may be ineffective. In some embodiments, position module 111 may be configured to determine the location of clothing or a diaper of infant 106.

In some embodiments, position module 111 may be configured to determine whether infant 106 is in a supine position. In some embodiments, position module 111 may be configured to determine whether the eyes of infant 106 are facing away from top-surface 7 of infant-supporting body 6. Position module 111 may be configured to determine whether an alarm and/or notification is warranted due to a mismatch in provided and/or recommended phototherapy vs. a determined presence, position, posture, and/or orientation of infant 106. Such an alarm and/or notification may, e.g., be presented via user interface 120. Alternatively, and/or simultaneously, the provided phototherapy may be adjusted automatically, e.g. by controlling light sources 11, responsive to a change in the determined presence, position, posture, and/or orientation of infant 106. Determinations by position module 111 may be used in other components of system 10.

In some embodiments, position module 111 may be configured to determine which light sources from the set of light sources 111 are in position to effectively provide phototherapy to infant 106, e.g. through using information conveyed by one or more imaging sensors. One or more imaging sensors, or cameras, may be arranged to capture output signals conveying visual information related to the position, posture, and/or orientation of infant 106 on top-surface 7. For example, a camera may capture an image of a top-view of infant 106, similar to the view depicted in FIG. 2. A lens (or other constituent component of a camera along the path from visual information to captured image) may insert, add, and/or superimpose a grid in/to/on the captured image. Alternatively, and/or simultaneously, a component external to the imaging sensor may be used to add grid information the captured image. For example, a grid may be depicted on top-surface 7. Such a grid may correspond in some predetermined and/or known fashion to a grid of light sources 11 underneath top-surface 7, as described in relation to FIG. 2. One or more determinations by position module 111 may be based on grid information and/or the captured image.

Light module 112 of system 10 in FIG. 3 may be configured to control one or more light sources 11 based on the determined position of infant 106 such that electromagnetic radiation emitted by one or more light sources 11 provides phototherapy for infant 106. Control by light module 112 may be based on individual light sources, one or more subsets of light sources, one or more groups of light sources, one or more rows and/or columns of light sources, and/or any combination thereof. Control by light module 112 may include control of the controllable level of intensity, the controllable direction and/or angle of illumination, the controllable selection of illumination spectra, and/or other controllable illumination characteristics and/or illumination parameters of one or more light sources 11. Control by light module 112 may be based on information from position module 111.

For example, light sources near the eyes of infant 106, when infant 106 is in a prone position, may be adjusted and/or turned down and/or off. Light sources that would emit radiation substantially on an area of infant 106 where no bare skin is exposed, may be adjusted and/or turned down and/or off. Light sources near the periphery of infant 106 and/or near the outline based on the position of infant 106 (such as, e.g., determined by projecting the volume of infant 106 onto top-surface 7) may be controlled and/or adjusted accordingly. Adjustments may include one or more of turning individual light sources or groups of light sources off and/or down, directing individual light sources or groups of light sources inwards such that the level of leaked electromagnetic radiation is affected and/or reduced), and/or other adjustments. Light sources that are determined to not be in position to effectively provide phototherapy for infant 106 may be controlled and/or adjusted accordingly.

Monitoring of the movements and changing positions of infant 106 may be used by light module 112 to adjust one or more light sources in keeping with the multiple goals of providing effective phototherapy to infant 106, keeping particular electromagnetic radiation out of the eyes of infant 106, and having an appropriately low level of leaked electromagnetic radiation.

Therapy module 113 of system 10 in FIG. 3 may be configured to determine a recommended phototherapy regimen for infant 106. A phototherapy regimen may be based on one or more of information related to the size/volume/weight of infant 106, information related to the age of infant 106, information related to previously administered phototherapy to infant 106, information related to medical parameters pertaining to the status of infant 106 (e.g. bilirubin measurements), stated and/or provided information from a user 108 or caregiver, clinician input, guidelines, charts, and/or other information. The recommended phototherapy regimen may in turn be used as a basis for operations and/or adjustments by light module 112.

FIG. 4 illustrates a method 400 for providing illumination for one or more cameras in a system. The operations of method 400 presented below are intended to be illustrative. In some embodiments, method 400 may be accomplished with one or more additional operations not described, and/or without one or more of the operations discussed. Additionally, the order in which the operations of method 400 are illustrated in FIG. 4 and described below is not intended to be limiting.

In some embodiments, method 400 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 400 in response to instructions stored electronically on an electronic storage medium. The one or more processing devices may include one or more devices configured through hardware, firmware, and/or software to be specifically designed for execution of one or more of the operations of method 400.

At an operation 402, an infant is supported on a top-surface of an infant-supporting body. In one embodiment, operation 402 is performed by an infant-supporting body similar to or substantially the same as infant-supporting body 6 (shown in FIG. 1 and described above).

At an operation 404, one or more output signals are generated conveying information related to a position of the infant on the top-surface of the infant-supporting body. In one embodiment, operation 404 is performed by a sensor similar to or substantially the same as sensor 142 (shown in FIG. 1 and described above).

At an operation 406, electromagnetic radiation is emitted through the top-surface of the infant-supporting body from a set of light sources. In one embodiment, operation 406 is performed by a set of light sources similar to or substantially the same as light sources 11 (shown in FIG. 1 and described above).

At an operation 408, the position of the infant on the top-surface of the infant-supporting body based on information from one or more sensors. In one embodiment, operation 408 is performed by a position module similar to or substantially the same as position module 111 (shown in FIG. 3 and described above).

At an operation 410, one or more subsets of light sources are controlled based on the determined position of the infant such that the emitted electromagnetic radiation provides phototherapy for the infant. In one embodiment, operation 410 is performed by a light module similar to or substantially the same as light module 112 (shown in FIG. 3 and described above).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A phototherapy system for an infant having a face and eyes, the system comprising:
    an infant-supporting body configured to support an infant on a top-surface thereof;
    one or more sensors that generate one or more output signals conveying information related to a position of the infant on the top-surface of the infant-supporting body;
    a set of light sources carried by the infant-supporting body, wherein the set of light sources are configured and arranged such that, responsive to activation of a subset of the set of light sources, electromagnetic radiation emitted by the subset of the set of light sources is guided through the top-surface of the infant-supporting body; and
    one or more processors configured to execute computer program modules, the computer program modules comprising:
        a position module configured to determine the position of an infant on the top-surface of the infant-supporting body, wherein the determination is based on information from the one or more sensors, and wherein the position includes a direction in which the eyes of the infant are facing; and
        a light module configured to control one or more subsets of light sources of the set of light sources based on the determined position of the infant and the direction in which the eyes of the infant are facing such that the emitted electromagnetic radiation provides phototherapy for the infant and such that the emitted electromagnetic radiation does not directly impinge on the eyes of the infant;
        wherein the light module is further configured to:
            turn down and/or turn off the one or more subsets of light sources proximate to the infant's eyes, in response to a determination that the eyes of the infant are facing the top surface of the infant supporting body; and
            cause the one or more subsets of light sources to emit electromagnetic radiation, in response to a determination that the eyes of the infant are facing away from the top surface of the infant supporting body.

2. The phototherapy system of claim 1, wherein the one or more sensors generate one or more output signals conveying information related to a size of the infant on the top-surface of the infant-supporting body, the system further comprising:
    a therapy module configured to determine a recommended phototherapy regimen for the infant based on information related to the size of the infant;
    wherein the light module is configured to control one or more subsets of light sources of the set of light sources by adjusting the level of electromagnetic radiation emitted by the one or more subsets of light sources of the set of light sources, wherein the adjustment by the light module is based on the recommended phototherapy regimen.

3. The phototherapy system of claim 1, wherein the one or more sensors include one or more imaging sensors configured to capture position information of the infant on the top-surface of the infant-supporting body, wherein the position module is furthermore configured to determine a three-dimensional position of the infant based on the captured position information from the one or more imaging sensors, and wherein the light module is further configured to control one or more light sources from the set of light sources based on the determined three-dimensional position.

4. The phototherapy system of claim 1, wherein the one or more sensors generate one or more output signals conveying information related to a level of leaked electromagnetic radiation emitted by the set of light sources such that the leaked electromagnetic radiation does not substantially contribute to the phototherapy for the infant;
    wherein the set of light sources are further configured to emit electromagnetic radiation in a range of directions, and wherein the light module is further configured to control directions of emissions of the set of light sources such that the level of leaked electromagnetic radiation is affected.

5. A method for controlling light sources of a phototherapy system configured to provide phototherapy to an infant having a face and eyes, wherein the phototherapy system includes an infant-supporting body having a top-surface, the method comprising:
    generating one or more output signals conveying information related to a position of the infant on the top-surface of the infant-supporting body;
    emitting electromagnetic radiation through the top-surface of the infant-supporting body from a set of light sources;

determining the position of the infant on the top-surface of the infant-supporting body based on information from one or more sensors, wherein the position includes a direction in which the eyes of the infant are facing; and controlling one or more subsets of light sources from the set of light sources based on the determined position of the infant and the direction in which the eyes of the infant are facing such that the emitted electromagnetic radiation does not directly impinge on the eyes of the infant;

wherein controlling the one or more subsets of light sources comprises:

turning down and/or turning off the one or more subsets of light sources proximate to the infant's eyes, in response to a determination that the eyes of the infant are facing the top surface of the infant supporting body; and causing the one or more subsets of light sources to emit electromagnetic radiation, in response to a determination that the eyes of the infant are facing away from the top surface of the infant supporting body.

6. The method of claim 5, further comprising:

generating one or more output signals conveying information related to a size of the infant on the top-surface of the infant-supporting body; and determining a recommended phototherapy regimen for the infant based on information related to the size of the infant, wherein controlling the one or more subsets of light sources from the set of light sources is accomplished by adjusting the level of electromagnetic radiation emitted by the one or more subsets of light sources of the set of light sources based on the recommended phototherapy regimen.

7. The method of claim 5, wherein the one or more sensors include one or more imaging sensors configured to capture position information of the infant on the top-surface of the infant-supporting body, the method further comprising:

determining a three-dimensional position of the infant based on the captured position information from the one or more imaging sensors;

wherein controlling the one or more subsets of light sources from the set of light sources is further based on the determined three-dimensional position.

8. The method of claim 5, further comprising:

generating one or more output signals conveying information related to a level of leaked electromagnetic radiation emitted by the set of light sources such that the leaked electromagnetic radiation does not substantially contribute to the phototherapy for the infant;

wherein the set of light sources are further configured to emit electromagnetic radiation in a range of directions, and wherein controlling the one or more subsets of light sources from the set of light sources includes controlling directions of emissions of the set of light sources such that the level of leaked electromagnetic radiation is affected.

9. A system configured to providing phototherapy to an infant having a face and eyes, the system comprising:

means for supporting an infant, the means for supporting having a top surface;

means for generating one or more output signals conveying information related to a position of the infant on the top-surface of the means for supporting the infant;

means for emitting electromagnetic radiation through the top-surface of the means for supporting the infant;

means for determining the position of the infant on the top-surface of the means for supporting the infant based on information from one or more sensors, wherein the position includes a direction in which the eyes of the infant are facing; and means for controlling the means for emitting electromagnetic radiation based on the determined position of the infant and the direction in which the eyes of the infant are facing such that the emitted electromagnetic radiation provides phototherapy for the infant and such that the emitted electromagnetic radiation does not directly impinge on the eyes of the infant;

wherein the means for controlling the means for emitting electromagnetic radiation is further configured to:

turn down and/or turn off the means for emitting electromagnetic radiation proximate to the infant's eyes, in response to a determination that the eyes of the infant are facing the top surface of the infant supporting body; and cause the means for emitting electromagnetic radiation to emit electromagnetic radiation, in response to a determination that the eyes of the infant are facing away from the top surface of the infant supporting body.

10. The system of claim 9, wherein the means for generating one or more outputs further generates one or more output signals conveying information related to a size of the infant on the top-surface of the means for supporting the infant, the system further comprising:

means for determining a recommended phototherapy regimen for the infant based on information related to the size of the infant, wherein the means for controlling the means for emitting electromagnetic radiation operates by adjusting the level of electromagnetic radiation, emitted by the means for emitting electromagnetic radiation, based on the recommended phototherapy regimen.

11. The system of claim 9, wherein the means for generating one or more output signals include one or more imaging sensors configured to capture position information of the infant on the top-surface of the means for supporting the infant, the system further comprising:

means for determining a three-dimensional position of the infant based on the captured position information from the one or more imaging sensors;

wherein operation of the means for controlling the means for emitting electromagnetic radiation is further based on the determined three-dimensional position.

12. The system of claim 9, wherein the means for generating one or more output signals further generates one or more output signals conveying information related to a level of leaked electromagnetic radiation emitted by the means for emitting electromagnetic radiation such that the leaked electromagnetic radiation does not substantially contribute to the phototherapy for the infant;

wherein the means for emitting electromagnetic radiation is further configured to emit electromagnetic radiation in a range of directions, and wherein the means for controlling the means for emitting electromagnetic radiation is further configured to control directions of emissions of the means for emitting electromagnetic radiation such that the level of leaked electromagnetic radiation is affected.

13. The system of claim 1, wherein the light module is further configured to turn down, turn off, and/or adjust the one or more subsets of light sources emitting radiation substantially on an area of the infant where no bare skin is exposed.

14. The method of claim 5, wherein controlling the one or more subsets of light sources comprises turning down, turning off, and/or adjusting the one or more subsets of light sources emitting radiation substantially on an area of the infant where no bare skin is exposed.

15. The system of claim 9, wherein the means for controlling the means for emitting electromagnetic radiation is further configured to turn down, turn off, and/or adjust the means for emitting electromagnetic radiation emitting radiation substantially on an area of the infant where no bare skin is exposed.

* * * * *